United States Patent
Obanda et al.

(10) Patent No.: US 9,414,598 B2
(45) Date of Patent: Aug. 16, 2016

(54) PROTECTING WOOD WITH STABILIZED BORON COMPLEXES

(75) Inventors: Diana N. Obanda, Baton Rouge, LA (US); Todd F. Shupe, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 1879 days.

(21) Appl. No.: 11/950,061

(22) Filed: Dec. 4, 2007

(65) Prior Publication Data

US 2008/0131717 A1 Jun. 5, 2008

Related U.S. Application Data

(60) Provisional application No. 60/872,941, filed on Dec. 5, 2006.

(51) Int. Cl.
| | |
|---|---|
| *B27K 3/52* | (2006.01) |
| *A01N 55/08* | (2006.01) |
| *A01N 55/00* | (2006.01) |
| *A01N 41/04* | (2006.01) |
| *A01N 59/14* | (2006.01) |
| *B27K 3/15* | (2006.01) |
| *B27K 3/16* | (2006.01) |
| *C08L 97/02* | (2006.01) |
| *C08L 83/02* | (2006.01) |

(52) U.S. Cl.
CPC ............... *A01N 55/00* (2013.01); *A01N 41/04* (2013.01); *A01N 59/14* (2013.01); *B27K 3/15* (2013.01); *B27K 3/16* (2013.01); *C08L 97/02* (2013.01); *C08L 83/02* (2013.01); *Y10T 428/662* (2015.04)

(58) Field of Classification Search
USPC ............... 428/537.1, 541; 427/393, 408, 440; 252/188; 106/619; 514/63
See application file for complete search history.

(56) References Cited

U.S. PATENT DOCUMENTS 6,541,038 B1 * 4/2003 Tanaka et al. .................. 424/618
6,821,631 B2 * 11/2004 Grantham et al. ............. 428/453

FOREIGN PATENT DOCUMENTS

JP 2694163 B2 * 12/1997

OTHER PUBLICATIONS

Chaoying Shoa et al., Studies on the Complexation of Boric Acid with Polyhydroxyl Compounds, 2001, Analytical Sciences, vol. 17, 1475-1478.*
John Wiley & Sons Inc., Naphthalene Derivatives, 2000, Kirk-Othmer Encyclopedia of Chemical Technology, 1-24.*
Donald Kuemmel and MG Mellon, Ultraviolet Absorptiometric Determination of Boron in Aqueous Medium Using Chromotropic Acid, 1957, Analytical Chemistry, vol. 29 No. 3, 378-382.*

(Continued)

*Primary Examiner* — Callie Shosho
*Assistant Examiner* — Patrick English

(57) ABSTRACT

Wood is treated to reduce or prevent biodeterioration using boron compounds. A significant portion of the active boron is retained within the wood when leached. Boric acid is complexed with water-soluble bifunctional polyhydroxyl aromatic compounds, and the boric acid bifunctional polyhydroxyl aromatic complex is deposited into wood treated with a silicate. The complexing agents comprise polyfunctional compounds, including at least two hydroxyl groups, and one or more separate acid groups.

11 Claims, 1 Drawing Sheet

(56) References Cited

OTHER PUBLICATIONS

Haruhiko Yamaguchi, Silicic Acid: boric acid complexes as wood preservatives, 2003, Wood Science Technology, vol. 37, 287-297.*

Sadrnezhaad et al., The effect of addition of Tiron as a surfactant on the microstructure of chemically deposited zinc oxide, Materials Science and Engineering: B, Mar. 15, 2006, vol. 128, Issues 1-3, pp. 53-57.*

Mazloumi et al., Studies on synthesis of alumina nanopowder from synthetic Bayer liquor, Materials Research Bulletin, Jun. 5, 2007, vol. 42, Issue 6, pp. 1004-1009.*

Revanasiddappa et al., Spectrophotometric determination of mosapride in pure and pharmaceutical preparations, 2007, Eclet. Quim., vol. 32, pp. 71-75.*

Lu, Chemical Coupling in Wood-Polymer Composites, Louisiana State University and Agricultural and Mechanical College Jun. 30, 2003, Chapter 2, p. 1.*

Yamaguchi, H., "Silicic acid/boric acid complexes as ecologically friendly wood preservatives," Forest Products Journal, vol. 55, No. 1, pp. 88-92 (2005).

Yamaguchi, H., "Silicic acid: boric acid complexes as wood preservatives. Ability of treated wood to resist termines and combustion," Wood Sci Technol, vol. 37, pp. 287-297 (2003).

* cited by examiner

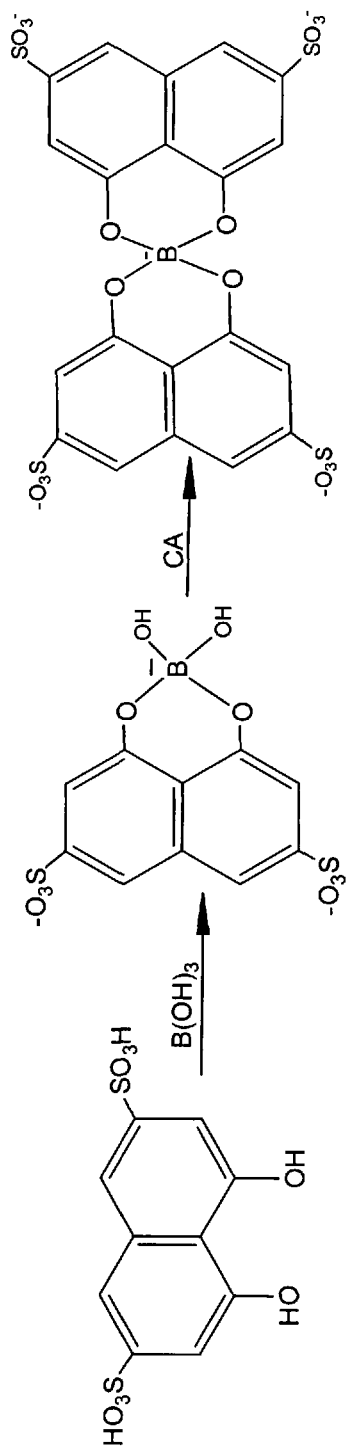

PROTECTING WOOD WITH STABILIZED BORON COMPLEXES

This application claims the benefit of U.S. Provisional Application Ser. No. 60/872,941, filed Dec. 5, 2006 under 35 U.S.C. §119(e).

This application pertains to a novel method and composition for protecting wood and wood products from biodeterioration using stabilized boron complexes. No sealant is required.

Wood and wood products may degrade when subjected to the natural environment, from causes such as bacteria, insects, and fungi. Costs from wood degradation have been as much as five billion dollars per year in the United States alone. Preservatives such as creosote, arsenic compounds, chromium compounds, and copper compounds have been used to prevent or reduce the effects of degradation.

Wood preservation using creosote or metals such as arsenic and chromium has fallen into disfavor because of environmental and health concerns.

The use of quaternary compounds of copper for wood preservation has proven inadequate for the broad spectrum activity that is required. Further, ammoniacal copper preservatives in wood products can cause massive corrosion to adjacent metal parts.

Zinc compounds also have been used, but they generally do not provide adequate protection from biodeterioration.

Recently, the wood industry has begun to replace preservatives based on chromium, arsenic, and the copper with materials that are more environmentally sound, such as boron, naturally occurring compounds, and organic biocides.

Borates show relatively low mammalian toxicity, while exhibiting a broad spectrum efficacy. However, past efforts to use boron compounds as wood preservatives have been limited by boron's tendency to leach. When boron is used as a wood preservative in high moisture environments, such as in outdoor settings, boron tends to leach out of the wood rapidly. However, if boron is bound completely within the wood structure, it tends to lose its effectiveness as a preservative.

Yamaguchi reports the use of silicic acid/boric acid complexes as wood preservatives. (*Forest Products Journal*, Vol. 55, pp. 88-92, 2005). (Also, see Yamaguchi, *Wood Science Technology*, Vol. 37, pp. 287-297, 2003). The formulations disclosed did not significantly reduce boron leaching when the treated wood was exposed to high moisture environments.

A number of strategies have been attempted to limit boron leaching, including painting and coating, using wood-bulking resins and water repellants, using organo-boron compounds, forming insoluble borate salts in situ within wood, combining boron biocides with non-biocidal additives that reduce leaching, forming metaloborates, ammoniacal and amine metaloborates, stabilizing boron-esters, using protein-borates, using borate and tannin autocondensates, polymerizing boron compounds with silicates or other monomers, vaporizing organic boron compounds and boric acid, and compressively deforming wood to reduce voids and hence moisture uptake. However, most of these methods have not been totally satisfactory.

For example, surface coatings, such as paints, waxes and resins, appear to provide primarily short term protection (depending on the thickness of the coat). Boronic acids and borinic acids, while somewhat effective, are too costly for commercial applications. The use of ammoniacal and amine metalo-borates is hampered by environmental concerns related to the use of high concentrations of ammonia. In addition to creating undesirable worker exposure problems in large-scale operations, these ammoniacol-materials appear to encourage mold growth on treated timber. The use of large molecules, such as tannin autocondensates and protein-borates as percursors, has not been successful because they do not effectively penetrate wood. Formaldehyde treatment of bulk wood also is not favored because formaldehyde can be toxic during handling of the wood.

U.S. Pat. No. 6,821,631 to Granthan discloses a method for treating wood using an alkali silicate solution, an alkali borate and boric oxide. An external sealant, for example a wax, is applied to the treated wood.

Attempts to bind borates with lower-solubility compounds within the wood have not generally been successful. For example, even though zinc borate (ZB) has good efficacy and leach resistance, its low solubility has made it impractical to pressure-treat solid wood with ZB.

Borate esters of various glycols have been used to treat wood. However, they are susceptible to hydrolysis Hydrolytically stable borate esters with biocidal properties, such as trialkylamine borates, trialkanolamine borates, monoalkanolamide borates, and esters of carbamates containing polyhydroxyl substitutes on the nitrogen atom, are not desirable because they tend to require organic solvents to penetrate wood, which presents environmental concerns when the solvents later vaporize.

There is an unfilled need for wood impregnated with an aqueous-soluble form of boron so that a high fraction of the boron will be retained within treated timber when exposed to moisture, while maintaining the boron's effectiveness as a wood preservative.

Wood and wood products that would benefit from such protection include wood and wood based materials used for interior construction such as furniture, wood framing, interior beams, flooring, millwork, and sillplates. Also, wood and wood based materials used for exterior construction, which may be subject to effects of weather, such as exterior walls, patio furniture, gazebos, decks, and utility poles could be protected.

We have discovered novel compositions and methods for treated wood using an aqueous boron solution that reduces or prevents biodeterioration wherein a significant portion of the active boron is retained within the wood even when exposed to moisture, without the need to coat the treated wood with a sealant. Wood is impregnated with a metal silicate. Boric acid, complexed with a water-soluble, bifunctional, polyhydroxyl aromatic compound, is deposited into silicate-treated wood. Without wishing to be bound by this theory, it appears that the metal silicate crosslinks or agglomerates with the boric acid complex. The complexing agents comprise polyfunctional compounds, including at least two hydroxyl groups, and at least one separate acid group. The hydroxyl groups may, e.g., be phenyl groups that are sterically positioned to facilitate complexing of the organic ligand with boron. The acid groups may be sulfonic, carboxylic, phosphoric, or other acid functional groups bound to an aromatic structure. The metal ion associated with the silicate anion may be $Li^+$, $Na^+$, $K^+$, $Rb^+$, $Mg^{2+}$ $NH_4^+$, or other monovalent or divalent cation.

Wood is treated with a combination of a polyhydroxyl acid, an alkali silicate, and boric acid to enhance retention of boron in wood. Formation of the complexes of boric acid and acidic polyhydroxyl ligands is favored with higher acidity chelate ligands. Species having two vicinal phenolic hydroxyl groups appear to form more stable borate complexes than those having other alcohol groups. In one embodiment chromotropic acid was used as the chelating agent. It showed high capacity to complex with boric acid over a wide pH range (2-10). Chromotropic acid ("CA") or other polyfunctional aromatic acid appears to act as a boron anchor, especially in an acidic medium.

We have found that a boric acid-CA complex is more effective in preventing deterioration of wood products when the complex is used in combination with a silicate. While not wishing to be bound by this theory, it appears that silicates act as matrix binders for the borate complex in voids in the wood. Though not wishing to be bound by this theory, it appears that alkali silicates raise the pH of the complex, and cause the boric acid/chromotropic acid complex to tend towards a 1:1 complex. As can be seen from the Figure, in a 1:1 complex the boric acid appears to be more available to protect the wood.

BRIEF DESCRIPTION OF THE DRAWING

The FIGURE depicts the reaction of boric acid with chromotropic acid.

As used throughout this application the terms "wood" and "wood products" refer to natural wood after it is harvested, in all forms, including paper products, particle board, plywood, fiberboard, oriented strand board, parallel strand lumber, laminated veneer lumber, glue laminated lumber, hardboard and other wood products.

While not wishing to be bound by this theory, it appears that when boron is impregnated into wood, it is bound to oxygens in —OH groups associated with cell walls. These boron-oxygen bonds are easily severed by water, and thus, boron is easily leached from wood. It appears that nearly all the boron in prior preparations has been lost via diffusion from the wood during the first few years in service. The rate of diffusion is a function of the boron concentration, temperature, and moisture levels. It appears that the threshold for diffusion occurs when the moisture level reaches approximately 20%.

In a preferred embodiment, an alkali silicate solution having a concentration between about 1 wt % and 10 wt %, preferably between 4 wt % and 6 wt %, is applied to a wood product, followed by a boron/bifunctional polyhydroxyl aromatic complex, having a concentration of boron between about 1 wt % and 10 wt %, preferably between 4 wt % and 6 wt %. The boron/bifunctional polyhydroxyl aromatic complex is made by reacting boric acid with a polyhydroxyl aromatic acid in a molar ratio between 1:2 to 4:1, aromatic: boric acid, preferably about 2:1. The bifunctional polyhydroxyl aromatic compounds have the general formula below:

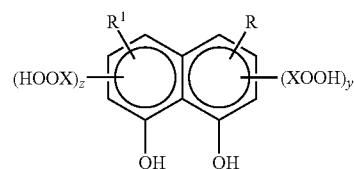

wherein X may be S=O, C, or PO(OH), y may be 0, 1, 2, or 3, and z may be 0, 1, 2, or 3, where y may be equal to or different from z, R may be H, $C_nH_{2n+1}$, $C_nH_{2n-1}$, $C_nH_{2n-3}$, or $C_nH_{2n-4}$, where n=1, 2, 3, or 4, and $R^1$ may be H, $C_nH_{2n+1}$, $C_nH_{2n-1}$, $C_nH_{2n-3}$, $C_nH_{2n-4}$, where n=1, 2, 3, or 4, where R may be the same as or different from R.

Alternatively, the polyhydroxyl aromatic compound may be

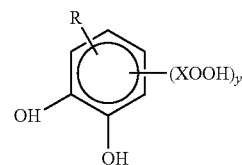

wherein X, y, and R are as above.

The XOOH group may be attached to any carbon having an available binding site, but preferably to a carbon which is meta to one of the phenolic groups.

In a preferred embodiment the polyhydroxyl complexing agent used was chromotropic acid (4,5-dihydroxy-2,7-naphthalenedisulfonic acid). Chromotropic acid ("CA") may form 1:1 or 1:2 complexes with boric acid, as shown in FIG. 1. It appears that the 1:1 complex was the principal active configuration in this embodiment.

Other ligands which may form stable water soluble esters with boron include Tiron (4,5-Dihydroxy-m-benzenedisulfonic acid) and other compounds having phenolic groups and an acid group on the same molecule, as shown below:

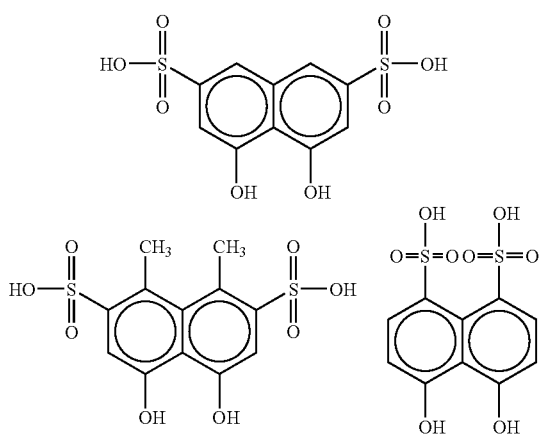

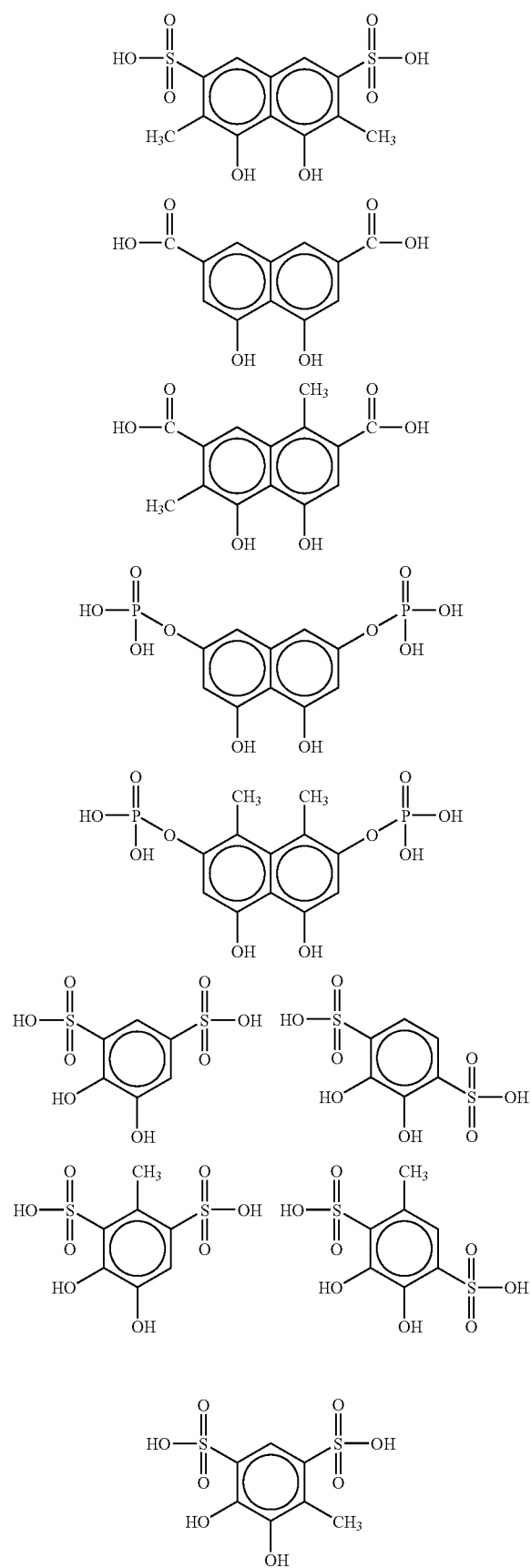

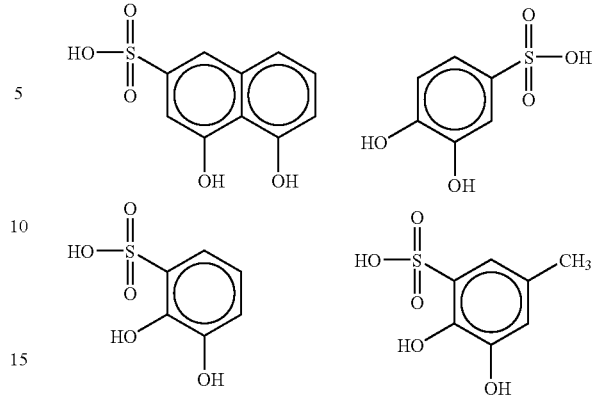

A sodium silicate solution is preferred to facilitate polymerization. Both boric acid and chromotropic acid appeared to reduce the pH of a sodium silicate solution below 10, which allowed polymerization. Thus, when the boric acid complex was added to sodium silicate, a polymer formed.

EXAMPLE 1

An aqueous solution containing about 5 wt % boric acid was added to an aqueous solution containing about 2% chromotropic acid. Southern yellow pine (*Pinus* sp.) wood cubes, about 15-20 mm on a side, were first air dried and then were impregnated under a slight vacuum with sodium silicate solution. The treated wood was again air dried before it was impregnated with the boric acid/chromotropic acid by first pulling a slight vacuum on the blocks, followed by adding the boric acid/chromotropic acid solution. Then the system was placed under a pressure of about 100 psi for 30 minutes. The wood cubes were again dried. The pH of all solutions was determined, and all treatment solutions were characterized by infrared spectrometry (IR). The treatment method was as otherwise described in AWPA E10-01 (AWPA, 2007).

EXAMPLE 2

Four tests were run on each of four different sets of samples:
Southern yellow pine wood cubes, about 15-20 mm on a side, were given different treatments as indicated below:
I. Treatments
 Treatment 1: untreated.
 Treatment 2: Boric acid (BA) only was impregnated into the wood cubes as follows: A wooden block was placed in 5 wt % boric acid solution in distilled water. The boric acid solution with the sample block was placed under a slight vacuum for about 10 minutes. This system was then pressurized to about 100 psi for about 30 minutes. The sample blocks were then dried at about 50° C. for about 2 hours.
 Treatment 3: Boric acid and Chromotropic acid (CA) were first reacted with each other, and the resulting complex was then impregnated into wood cubes as follows: A wooden block was placed in a treatment solution containing about 5% boric acid and about 2% chromotropic acid solutions in distilled water. This solution was then placed under a slight vacuum for 10 minutes. Then the system was placed under pressure of about 100 psi for 30 minutes. The sample blocks were then dried at about 50° C. for about 2 hours.

Treatment 4: An aqueous solution containing about 5 wt % boric acid was added to an aqueous solution containing about 2% chromotropic acid. Wood cubes, about 15-20 mm on a side, were first air dried and then were impregnated under a slight vacuum with sodium silicate solution. The treated wood was again air dried before it was impregnated with the boric acid/chromotropic acid by first pulling a slight vacuum on the blocks, followed by adding the boric acid/chromotropic acid solution. Then the system was placed under a pressure of about 100 psi for 30 minutes. The wood cubes were again dried.

II. Tests:

The following tests were performed on each of the samples described above:
1. Leaching
2. Brown Rot on both leached and unleached samples
3. White Rot on both leached and unleached samples
4. Termites on both leached and unleached samples Prior to testing, all samples were dried and conditioned at 50° C. for two weeks.

All data were evaluated for statistical significance using a Student's t-test. Data were considered statistically different when $p<0.05$.

TABLE 1

Treatments and total number of samples treated

| Test | Untreated controls | Boric acid only | Boric acid + Chromotropic acid | Boric acid + Chromotropic acid + Sodium silicate |
|---|---|---|---|---|
| Leaching | 5 | 50 | 50 | 50 |
| White rot | 13 | 13 | 13 | 13 |
| Brown rot | 13 | 13 | 13 | 13 |

EXAMPLE 3

Leaching Test

Accelerated leaching tests were performed according to AWPA E11-97 (AWPA, 2003). Four Southern yellow pine (*Pinus* sp.) samples were leached, each in its own leaching flask. At the end of each leaching period, the leachate was collected and the samples were air dried for two weeks. The amount of boron retained in the wood was determined by inductive coupled plasma (ICP) spectrometry after boron was extracted with hydrochloric acid from the ground wood.

Retention of boron in the samples before leaching is shown in Table 2.

TABLE 2

Mean values of the initial boron retention in ppm.

| Test | Boric acid | Boric acid + Chromotropic acid | Boric acid + Chromotropic acid + Sodium silicate |
|---|---|---|---|
| Leaching | 2075.0[a] (2.19)[b] | 2127.57 (1.22) | 2123.73 (2.22) |
| White rot | 2225.43 (1.27) | 2217.34 (3.27) | 2119.34 (1.21) |
| Brown rot | 2227.31 (3.27) | 2219.23 (1.27) | 2219.23 (1.21) |

[a](average of three samples)
[b](standard deviations)

Table 3 shows the concentration of boron after leaching.

TABLE 3

Mean of boron retained in wood in ppm (std. dev).
(Each value is the mean of three samples)

| Leaching duration (days) | Boric acid only (std. dev) | Boric acid + Chromotropic acid (std. dev) | Boric acid + Chromotropic acid + Sodium silicate (std. dev) |
|---|---|---|---|
| 0 (Not unleached) | 2075.0 (80.18) | 2127.57 (136.04) | 2123.73 (130.20) |
| 6 hours | 1005.00 (125.2) | 1132.21 (149.51) | 1188.43 (71.34) |
| 24 hours | 737.13 (40.85) | 609.27 (20.87) | 1091.19 (69.55) |
| 2 days | 99.32 (17.84) | 472.05 (56.84) | 940.85 (56.06) |
| 4 days | 25.37 (2.81) | 454.61 (39.74) | 956.114 (70.46) |
| 6 days | 2.908 (0.61) | 280.78 (23.09) | 942.58 (54.20) |
| 8 days | 2.941 (0.83) | 222.80 (20.73) | 890.58 (37.21) |
| 10 days | 2.89 (0.79) | 205.67 (13.47) | 897.49 (38.85). |
| 12 days | 2.79 (0.53) | 183.65 (12.39) | 898.83 (32.16) |
| 14 days | 2.8 (0.82) | 171.78 (12.56) | 879.89 (43.76) |

Some of the differences seen in retention of boron among the samples were believed to be due to minor size difference of the wood cubes used. There was a high rate of reduction in boron levels within the first two days of leaching for all samples, which is believed to have been due to leaching of boron deposited on surfaces of the cubes. Samples treated with only boric acid lost most of their boron within 6 hours. Samples treated with a combination of boric acid and chromotropic acid retained 8.03% of the boron at the end of the leaching period. The combination of boric acid and chromotropic acid with sodium silicate had the highest retention of boron, at about 41.89%.

EXAMPLE 4

Decay Test

Decay tests were conducted on wood blocks, both leached and unleached. Samples were halved, with one group subjected to weathering and the other group maintained unweathered. Both sets of samples were subjected to a soil block culture test according to the AWPA E10-01 method. For each block, the percentage of mass loss was determined. These samples were allowed to decay for 12 weeks for brown rot decay and for 16 weeks for white rot decay. Table 4 provides a summary of these results.

TABLE 4

Results of the decay test - % mass loss.

| Decay test | Untreated controls (std. dev) | Boric acid only (std. dev) | | Boric acid + Chromotropic acid (std. dev) | | Boric acid + Chromotropic acid + Sodium silicate (std. dev) | |
| --- | --- | --- | --- | --- | --- | --- | --- |
| | | Not leached | leached | Not leached | leached | Not leached | leached |
| White rot | 18.31 (3.11) | 2.51 (0.51) | 16.59 (2.19) | 3.23 (1.29) | 12.91 (1.71) | 4.23 (1.29) | 5.99 (1.17) |
| Brown rot | 21.32 (2.06) | 3.21 (0.22) | 18.88 (2.30) | 4.32 (1.21) | 12.61 (4.12) | 5.56 (1.89) | 8.6 (2.12) |

Decay test results shown in Table 4 show a significant and substantial difference between untreated controls and the unleached samples for all treatments. Samples treated with boric acid that were leached provided no significant decay resistance. Samples treated with boric acid and chromotropic acid (only) that were leached did not retain sufficient boron to prevent significant decay. Samples treated with all three compounds, which showed the greatest boron retention, provided significantly and substantially better resistance to decay after leaching.

Termite Testing.

The wood cubes also were subjected to a termite mortality test (*Coptotermes formosanus*). The results are shown below in Table 5.

TABLE 5

Termite mortality (%)

| Treatment | Leached samples | Unleached |
| --- | --- | --- |
| 1. Untreated samples | 5.3 | 4.1 |
| 2. (boric acid only) | 95.2 | 4.3 |
| 3. (boric acid + chromotropic acid) | 95.2 | 4.7 |
| 4. (boric acid + chromotropic acid + sodium silicate) | 72.3 | 43.1 |

Results showed the boron-CA-SS treated wood cubes after leaching were effective. However, treatment with boron only or with boron plus chromotropic acid (only) also provided adequate protection against termites.

The complete disclosures of all references cited in this specification, including the 60/872,941 priority application, are hereby incorporated by reference. In the event of an otherwise irreconcilable conflict, however, the present specification shall control.

We claim:

1. A method for protecting wood; said method comprising treating the wood with a silicate, boric acid, and a complexing agent; wherein
   c. the complexing agent comprises chromotropic acid (4,5-dihydroxy-2,7-naphthalenedisulfonic acid).

2. The method as in claim 1, wherein said treating occurs at a pH below about 10.

3. The method as in claim 1, wherein no external sealant is applied to the wood.

4. The method as in claim 1, wherein the silicate is associated with a cation selected from the group consisting of $Li^+$, $Na^+$, $K^+$, $Rb^+$, $Mg^{2+}$, $Ca^{2+}$, $NH_4^+$, and other monovalent and divalent cations.

5. The method as in claim 1, wherein said treating sufficiently binds boron to the wood that at least about 40% of the boron atoms will remain in the wood after the wood is subjected to 14 days of aqueous leaching.

6. A treated wood product comprising wood treated with a silicate, boric acid, and a complexing agent; wherein
   c. said complexing agent comprises chromotropic acid (4,5-dihydroxy-2,7-naphthalenedisulfonic acid).

7. The treated wood as in claim 6, wherein said treated wood has a pH below about 10.

8. The treated wood as in claim 6, wherein said treated wood has no external sealant.

9. The treated wood as in claim 6, wherein said silicate is associated with a cation selected from the group consisting of $Li^+$, $Na^+$, $K^+$, $Rb^+$, $Mg^{2+}$, $Ca^{2+}$, $NH_4^+$, and other monovalent and divalent cations.

10. The treated wood as in claim 6, wherein said treating sufficiently binds boron to said wood that at least about 40% of the boron atoms will remain in the wood after the wood is subjected to 14 days of aqueous leaching.

11. A wood product comprising a product selected from the group consisting of lumber, paper, particle board, plywood, oriented strand board, parallel strand lumber, laminated veneer lumber, glue laminated lumber, hardboard and fiberboard, wherein said wood product comprises the treated wood as in claim 6.

* * * * *